(12) United States Patent
Weber et al.

(10) Patent No.: US 6,352,528 B1
(45) Date of Patent: Mar. 5, 2002

(54) ABSORBENT ARTICLES INCLUDING HIDDEN GRAPHICS

(75) Inventors: Shirlee Ann Weber, Neenah; Lisa Ann Dimitrijevs, Appleton; Thomas Michael Gage, Hortonville; Christopher Peter Olson, Neenah, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/444,081

(22) Filed: Nov. 22, 1999

(51) Int. Cl.[7] .................. A61F 13/56; A61F 13/58; A61F 13/62

(52) U.S. Cl. ............. 604/385.03; 604/387; 604/389; 604/390; 604/391; 604/385.01

(58) Field of Search ............. 604/361, 385.03, 604/386, 387, 389–391, 385.01

(56) References Cited

U.S. PATENT DOCUMENTS

| | | | |
|---|---|---|---|
| 3,842,837 A | * 10/1974 | Sward | 128/284 |
| 4,315,508 A | 2/1982 | Bolick | |
| 4,615,695 A | 10/1986 | Cooper | 604/385 A |
| 4,662,875 A | 5/1987 | Hirotsu et al. | |
| 4,663,220 A | 5/1987 | Wisneski et al. | |
| 4,701,170 A | 10/1987 | Wilson et al. | |
| 4,701,176 A | 10/1987 | Wilson et al. | |
| 4,704,116 A | 11/1987 | Enloe | |
| 4,761,318 A | 8/1988 | Ott et al. | 428/85 |
| 4,770,656 A | 9/1988 | Proxmire et al. | 604/393 |
| 4,834,742 A | 5/1989 | Wilson et al. | 604/389 |
| 4,894,060 A | 1/1990 | Nestegard | 604/391 |
| 4,936,840 A | 6/1990 | Proxmire | 604/385.2 |
| 4,940,464 A | 7/1990 | Van Gompel et al. | |
| 5,032,122 A | 7/1991 | Noel et al. | 604/391 |
| 5,046,272 A | 9/1991 | Vogt et al. | |
| 5,062,839 A | 11/1991 | Anderson | 604/389 |
| 5,087,253 A | 2/1992 | Cooper | 604/385.1 |
| 5,096,424 A | 3/1992 | Carlberg | |
| 5,104,116 A | 4/1992 | Pohjola | |
| 5,133,707 A | 7/1992 | Rogers et al. | |
| 5,224,405 A | 7/1993 | Pohjola | |
| 5,226,992 A | 7/1993 | Morman | |
| 5,235,515 A | 8/1993 | Ungpiyakul et al. | |
| 5,256,231 A | 10/1993 | Gorman et al. | 156/178 |

(List continued on next page.)

FOREIGN PATENT DOCUMENTS

| | | | |
|---|---|---|---|
| EP | 0 217 032 B1 | 2/1992 | |
| EP | 0 756 855 A1 | 2/1997 | |
| EP | 0 570 980 B1 | 7/1997 | A61F/13/15 |
| GB | 1 520 740 | 8/1978 | |
| GB | 2 267 024 A | 11/1993 | A61F/13/66 |
| WO | WO 95/18589 A1 | 7/1995 | A61F/13/15 |
| WO | WO 98/21035 A1 | 5/1998 | |
| WO | WO98/21134 A1 | 5/1998 | |
| WO | WO 98/21135 A1 | 5/1998 | |
| WO | WO 98/21136 A1 | 5/1998 | |
| WO | WO 98/21137 A1 | 5/1998 | |
| WO | WO 99/32384 A1 | 7/1999 | |
| WO | WO 99/65441 A1 | 12/1999 | A61F/13/15 |

*Primary Examiner*—Dennis Ruhl
*Assistant Examiner*—Michael Bogart
(74) *Attorney, Agent, or Firm*—Thomas M. Gage

(57) ABSTRACT

A disposable and refastenable pant includes hidden graphics. When the fastening system is engaged, such as would be the case during use, the hidden graphics are not directly visible upon inspection of the interior and exterior surfaces of the garment. The hidden graphics become visible when the fasteners are disengaged from one another. For training pants, the hidden graphics can be used by the caregiver or parent as a motivational and educational instrument to improve the speed and quality of the total toilet training process.

67 Claims, 9 Drawing Sheets

U.S. PATENT DOCUMENTS

| | | |
|---|---|---|
| 5,275,588 A | 1/1994 | Matsumoto et al. |
| 5,326,612 A | 7/1994 | Goulait ........................ 428/100 |
| 5,380,313 A | 1/1995 | Goulait et al. .............. 604/391 |
| 5,458,590 A | 10/1995 | Schleinz et al. |
| 5,527,302 A | 6/1996 | Endres et al. ............ 604/385.1 |
| 5,531,731 A * | 7/1996 | Brusky ........................ 604/358 |
| 5,560,798 A | 10/1996 | Brusky |
| 5,595,567 A | 1/1997 | King et al. .................. 604/391 |
| 5,612,118 A | 3/1997 | Schleinz et al. |
| 5,616,394 A | 4/1997 | Gorman et al. ............... 428/99 |
| H1674 H | 8/1997 | Ames et al. ................. 604/389 |
| 5,655,843 A | 8/1997 | Conrad et al. .............. 383/204 |
| 5,725,382 A | 3/1998 | Walter et al. |
| 5,766,389 A | 6/1998 | Brandon et al. |
| 5,772,960 A | 6/1998 | Ito et al. ..................... 604/390 |
| 5,782,819 A | 7/1998 | Tanzer et al. ............ 604/385.1 |
| 5,785,699 A | 7/1998 | Schmitz et al. ............. 604/391 |
| 5,795,350 A | 8/1998 | Schmitz ....................... 604/391 |
| 5,818,719 A | 10/1998 | Brandon et al. |
| 5,851,205 A | 12/1998 | Hisada et al. ............... 604/390 |
| 5,891,122 A | 4/1999 | Coates .................... 604/385.1 |
| 5,897,545 A | 4/1999 | Kline et al. .................. 604/386 |
| 5,897,546 A | 4/1999 | Kido et al. .................. 604/391 |
| 5,906,008 A | 5/1999 | Heki et al. ...................... 2/400 |
| 5,967,665 A * | 10/1999 | MacDonald et al. ........ 383/207 |
| 5,997,521 A | 12/1999 | Robles et al. ............ 604/385.2 |
| 6,022,430 A | 2/2000 | Blenke et al. |
| 6,086,571 A | 7/2000 | Guevara et al. ......... 604/385.2 |
| 6,113,717 A | 9/2000 | Vogt et al. .................. 156/73.1 |
| 6,210,388 B1 | 4/2001 | Widlund et al. ............ 604/390 |
| 6,213,991 B1 | 4/2001 | Kling et al. ........... 604/385.01 |

* cited by examiner

ABSORBENT ARTICLES INCLUDING HIDDEN GRAPHICS

BACKGROUND OF THE INVENTION

The present invention relates to absorbent articles which are adapted to contain body exudates. More particularly, the invention pertains to pant-like disposable absorbent articles with refastenable seams and hidden graphics, packages of such disposable absorbent articles, and methods of making such disposable absorbent articles.

The age at which little boys and girls begin the toilet training process varies significantly. Some children may start the toilet training process as early as the age of fifteen months, while others may not be ready until after the age of two years. The age at which children begin this training process is dependent upon many factors, some of which are psychological, some physiological, and some unique to the individual child or their environment.

The toilet training process embraces a number of aspects, not all of which apply to each child. One aspect of the total toilet training process is the change from diapers to training pants to help the child understand that he or she should now use the toilet just like grownups. Another aspect of the total toilet training process includes parental or caregiver instruction as a positive encouragement and reinforcement to the child that he or she should now be using a toilet instead of diapers. Although the use of training pants and positive encouragement from the parent or caregiver have been helpful in the toilet training process, there is still much room for improvement. Specifically, parents and caregivers are still searching for easier and quicker ways to guide their children successfully through the toilet training process.

Many caregivers and parents have difficulty in determining the readiness of a child to begin the toilet training process, and underestimate the difficulty of teaching the toilet training process to young children. If a child does not respond to an initial toilet training instruction or introduction, the caregiver or parent can be at a loss for finding techniques, methods, or teaching tools to encourage the child to master the art of toilet training. Thus, while various teaching tools such as books, videotapes, charts with stickers, personalized toilets, and interactive toilet training kits are available, there remains a need for new and improved educational and motivational mechanisms to facilitate the toilet training process.

SUMMARY OF THE INVENTION

In response to the above-referenced unfulfilled need in the art, a new disposable absorbent article has been discovered. The absorbent article is in the form of a refastenable pant with hidden graphics. The fastening system of the pant can be repeatedly fastened, unfastened and refastened. When the fastening system is engaged, such as would be the case during use and when manufactured in a prefastened condition, the hidden graphics are not directly visible upon inspection of the inner and outer surfaces of the garment. Rather, the hidden graphics become visible only when the fasteners are disengaged from one another. The hidden graphics can be used by the caregiver or parent as a motivational and educational instrument to improve the speed and quality of the total toilet training process.

In one embodiment, the present invention pertains to an absorbent article including an absorbent chassis defining longitudinal and transverse axes, opposite inner and outer surfaces, first and second longitudinally spaced waist regions, and a crotch region which extends between and interconnects the waist regions. The first waist region defines a pair of transversely opposed side panels. The absorbent article also includes first and second fastening components disposed on the side panels, and at least one mating fastening component disposed in the second waist region. The fastening components are adapted to releasably engage the mating fastening component, thus forming an overlap region of the first and second waist regions. A graphic is disposed in the overlap region in the second waist region, separate from and transversely outward from the at least one mating fastening component, to define a hidden graphic.

In another embodiment, the present invention pertains to an absorbent article including an absorbent chassis with a pair of transversely opposed side panels in the first waist region. First and second fastening components are disposed on the side panels, and at least one mating fastening component is disposed in the second waist region. The fastening components releasably engage the mating fastening component to form an overlap region of the first and second waist regions. Additionally, a graphic is disposed in the overlap region and on the inner surface of one of the side panels to define a hidden graphic.

In this particular embodiment, the graphic can be disposed on one or both of the first and second fastening components, and/or disposed in close proximity to and transversely inward from one of the fastening components.

In a further embodiment, the present invention pertains to an absorbent article with a fastening system including first and second fastening components disposed in the first waist region and first and second mating fastening components disposed in the second waist region. At least one of the mating fastening components includes a freeform graphic. The first and second fastening components are substantially the same size or larger than the freeform graphic and substantially the same size or larger than the first and second mating fastening components. In this way, the freeform graphic forms a hidden graphic when the fastening components are centrally positioned relative to and engaged with the mating fastening components.

As used here, the term "freeform graphic" refers to all forms of graphics except those that form all or part of an array of identical or similar discrete graphic elements defining transversely oriented columns. Freeform graphics can comprise text messages and/or pictorial images, but as noted exclude position indicators in the form of transversely oriented graphic arrays. Such graphic arrays have been employed on disposable absorbent articles for use as position indicators for fastening tapes. Graphic arrays using identical graphic elements, similar-size graphic elements, and similar-shaped graphic elements as position indicators are disclosed in U.S. Pat. No. 4,662,875 issued May 5, 1987 to Hirotsu et al.; U.S. Pat. No. 5,133,707 issued Jul. 28, 1992 to Rogers et al.; and U.S. Pat. No. 5,275,588 issued Jan. 4, 1994 to Matsumoto et al.

In a still further embodiment, the present invention pertains to an absorbent article with a fastening system including first and second fastening components disposed on the inner surface in the back waist region and first and second mating fastening components disposed on the outer surface in the front waist region. Each of the mating fastening components has a length dimension that is equal to or greater than a width dimension. At least one of the mating fastening components includes a freeform graphic that forms a hidden graphic when the fastening components are engaged with the mating fastening components.

In yet another embodiment, the present invention pertains to an absorbent article defining a longitudinal axis, a transverse axis, front and back longitudinally spaced waist regions, and a crotch region which extends between and interconnects the waist regions. The absorbent article includes an absorbent chassis and front and back elastic side panels extending transversely outward from the absorbent chassis in the front and back waist regions. A mechanical fastening system includes first and second fastening components disposed on the front elastic side panels and first and second, mating fastening components disposed on the back elastic side panels. A graphic is located on at least one of the fastening components or the mating fastening components and forms a hidden graphic when the fastening components are engaged with the mating fastening components.

The fastening components and the mating fastening components form refastenable seams for securing the first and second waist regions together. The refastenable seams allow the product to be either pulled on like a pant or applied like a diaper. If the training pant becomes soiled during use, the first and second fastening components can be disengaged from the first and second mating fastening components to easily remove the training pant from the waist of the wearer with reduced risk of undesirably soiling the clothes or legs of the wearer. Further, the fastening components can also be easily disengaged to inspect the training pant for possible soiling. Thus, the training pant is configured to be pulled on or off over the hips of the wearer such as conventional training pants and can be readily applied or removed by disengaging the fasteners similar to conventional diapers. Moreover, the fastening components can be repositioned if necessary after the training pant has been pulled on over the legs and hips of the wearer.

The hidden graphics can provide a motivational and educational mechanism for the caregiver or parent to use to improve the speed and quality of the toilet training process. The hidden graphics can comprise text messages consisting of alphanumeric symbols, pictorial images consisting of pictures, or both text messages and pictorial images. In particular embodiments, the hidden graphics can be formed by graphics disposed on the fastening components and/or the mating fastening components. Alternatively, the hidden graphics can be formed by graphics disposed on other components of the absorbent article, such as the outer cover, the bodyside liner, side panels, or the like, and on either the inner surface or the outer surface of the absorbent article. In either case, the hidden graphics do not become visible to the child or caregiver until the fastening components are disengaged to expose the facing surfaces of the absorbent article in the overlapping regions. The hidden graphics, when they become visible, can provide opportunities for positive interaction to make the toilet training process more enjoyable for the child and caregiver. The hidden graphics can provide educational opportunities as well.

In certain embodiments, two or more graphics on the absorbent article can be related in subject matter. As used herein, the phrases "subject matter relationship" and "related in subject matter" refer to the situation where the subject matter of one graphic is the same as or is linked to the subject matter of another graphic. The subject matter relationship can be between two or more text messages, between two or more pictorial images, or between a combination of one or more text messages and one or more pictorial images. By way of example, two text messages are considered related in subject matter where the messages: are identical; jointly form a sentence, thought, or action such as "attach" and "here"; each refer to one and the other of two items that are commonly associated with one another, such as "bat" and "ball," "Big" and "Kid," "Big" and "Girl," or "Big" and "Boy"; jointly present a question and answer; or the like. Similarly, two pictorial images are considered related in subject matter where the images are identical; separately illustrate different sizes, shapes, colors of a common object; each illustrate one and the other of two objects that are commonly associated with one another, such as the moon and stars; jointly illustrate geometrically mating or engaging elements such as a triangle and a triangularly-shaped aperture, or two halves of a zipper; each illustrate one part of a multipart picture; or the like. Likewise, a text message and a pictorial image are considered to have a subject matter relationship where the text names, defines or describes the image; or the like.

To facilitate fastening and refastening of the fastening system, the fastening components of the absorbent article can comprise text messages or pictorial images that indicate where to attach the fasteners. Moreover, the first and second fastening components and the first and second mating fastening components can each comprise text messages or pictorial images that indicate where to attach the fastening components and the mating fastening components. In one embodiment, for instance, the first and second fastening components and the first and second mating fastening components each comprise an identical pictorial image that denotes proper attachment zones.

In particular embodiments, the absorbent article can include both hidden graphics and outer cover graphics, which can but need not necessarily be related in subject matter. In one embodiment, for instance, an absorbent article defines longitudinal and transverse axes, first and second longitudinally spaced waist regions, and a crotch region which extends between and interconnects the first and second waist regions. The absorbent article includes an absorbent chassis with an outer cover and an outer cover graphic. First and second fastening components comprising mechanical fastening elements are disposed in the first waist region, and at least one mating fastening component is bonded to the outer cover in the second waist region. The mating fastening component is formed of mechanical fastening elements that are adapted to releasably engage the fastening components. In one embodiment, at least one of the fastening components or the at least one mating fastening component include a graphic defining a hidden graphic. As noted, the outer cover graphic can be related in subject matter to the hidden graphic.

Outer cover graphics are directly visible on the exterior surface of the absorbent article and have been extremely appealing to children. Moreover, parents and caregivers can use outer cover graphics as educational and motivational tools to advance the toilet training process. By relating the hidden graphic to the outer cover graphic, many new educational and motivational opportunities are available to enhance the toilet training process. The outer cover graphic typically comprises a pictorial image, and the hidden graphic may comprise either a text message or a pictorial image. Optionally, the outer cover graphic and the hidden graphic may comprise separate parts of a complete pictorial image that is only revealed by disengaging the fastening components.

The refastenable seams are formed when the first and second fastening components are engaged with at least one mating fastening component, which may comprise first and second mating fastening components. As used herein, the term refastenable seam is limited to those portions of the fastening components that releasably engage one another.

Thus, finger tab portions, anchoring portions, other materials that do not releasably fasten together, and other non-fastening portions of the first and second fastening components and first and second mating fastening components do not constitute part of the refastenable seam.

The refastenable seams are desirably relatively thin, narrow and flexible to afford the look and feel of a cloth garment. Thus, in particular embodiments, the refastenable seams have a length-to-width ratio of about 2 or greater, such as about 2 to about 25, particularly about 5 or greater, such as about 5 to about 8. The refastenable seams define a length dimension and a width dimension that is perpendicular to the length dimension. For a child of about 9 to about 15 kilograms (20–34 lbs.), for example, the length dimension is desirably from about 5 to about 13 centimeters, such as about 10 centimeters, and the width dimension is desirably from about 0.5 to about 3 centimeters, such as about 2 centimeters. Desirably although not necessarily, the length dimension can be aligned generally parallel to the longitudinal axis of the absorbent article and the width dimension can be aligned generally parallel to the transverse axis of the absorbent article. The term "generally parallel" as used herein refers to an angle within about 35 degrees or less of the referenced axis, and more particularly within about 20 degrees or less of the referenced axis.

The fastening components can comprise any refastenable fasteners suitable for absorbent articles, although desirably comprise mechanical fastening elements rather than adhesive fastening elements for improved performance. Suitable mechanical fastening elements may be provided by interlocking geometric shaped materials, such as hooks, loops, bulbs, mushrooms, arrowheads, balls on stems, male and female mating components, buckles, snaps, or the like. In particular embodiments, the fastening components and mating fastening components comprise hook-and-loop fastening elements. One skilled in the art will recognize that the shape, density and polymer composition of the hooks and loops may be selected to obtain the desired level of securement between the fastening components and the mating fastening components. A more aggressive hook material may comprise a material with a greater average hook height, a greater percentage of directionally-aligned hooks, or a more aggressive hook shape.

As disclosed in copending U.S. patent application Ser. No. 60/112,709, filed on Dec. 18, 1998 by C. P. Olson et al. and titled "Absorbent Articles Having Differential Strength Refastenable Seam," the refastenable seam may include one or more main refastenable attachment zones and one or more enhanced refastenable attachment zones. The main and enhanced refastenable attachment zones may be constructed to provide differential levels of securement, and particularly augmented levels of securement at locations which are subject to greater levels of separation forces.

As disclosed in copending U.S. patent application Ser. No. 60/112,775, filed on Dec. 18, 1998 by C. P. Olson and titled "Absorbent Articles Having Hinged Fasteners," the refastenable seam may comprise individual fastening materials with narrow spacings therebetween. The narrow spacings provide a desirable hinge to improve fit and securement of the fastening components.

The disclosed absorbent articles are adapted to be worn adjacent to the body of a wearer to absorb and contain various exudates discharged from the body. The absorbent articles are desirably pre-fastened during manufacture to provide a pant-like product for the user. The product can then be pulled on like a conventional training pant, and subsequently checked or removed with the ease of a diaper-like product. Moreover, the product may be applied like a diaper rather than like a pant. Supplemental releasable fastening means such as frangible point bonds may be employed to maintain the absorbent article in a pant configuration until the user intentionally disengages the fasteners.

The fastening system allows for easy inspection of the interior of the pant-like product. If necessary, the fastening system also allows the pant to be removed quickly and easily. This is particularly beneficial when the pant contains messy excrement. If desired, the caregiver can completely remove the pant-like product and replace it with a new one without having to remove the child's shoes and clothing. The present fastening system may be used with a wide variety of absorbent products, including training pants, swimpants, diapers, incontinence garments, or other garments using mechanical or adhesive fasteners.

The present invention also pertains to a package of absorbent articles with hidden graphics. The package includes a bag defining an interior space and a plurality of prefastened absorbent articles disposed within the interior space. The prefastened absorbent articles define first and second longitudinally spaced waist regions and a crotch region which extends between and interconnects the waist regions. The absorbent articles include fastening components disposed in the first waist region and at least one mating fastening component disposed in the second waist region. The first and second waist regions overlap one another to define an overlap region. The fastening components are releasably engaged with the mating fastening component, and a graphic is disposed in the overlap region to define a hidden graphic.

The present invention also pertains to a method of making packages of absorbent articles. In one embodiment, the method includes: providing an absorbent article comprising an absorbent chassis defining a longitudinal axis, a transverse axis, first and second longitudinally spaced waist regions, and a crotch region which extends between and interconnects the waist regions, the absorbent chassis comprising a bodyside liner, an outer cover, and an absorbent assembly disposed between the bodyside liner and the outer cover; creating a graphic on the absorbent chassis; attaching first and second fastening components to the absorbent chassis in the first waist region; attaching at least one mating fastening component to the absorbent chassis in the second waist region, the fastening components adapted to releasably engage the at least one mating fastening component; releasably engaging the first and second fastening components with the at least one mating fastening component to define an overlap region of the first and second waist regions, the graphic disposed in the overlap region to define a hidden graphic; assembling a plurality of absorbent articles having hidden graphics; and placing the assemblage of absorbent articles having hidden graphics in a bag.

A more detailed description of the construction and design of one form of training pant can be found in U.S. Pat, No. 4,940,464 issued Jul. 10, 1990 to Van Gompel et al., which is incorporated herein by reference. The Van Gompel et al. patent describes various materials of which the training pant can be made, and a method of constructing a training pant.

Definitions

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on" and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move. Force is expressed in grams per unit area.

"Graphic" refers to any design, pattern, or the like that is visible on an absorbent article, and specifically includes text messages and pictorial images.

"Hidden graphic" refers to a graphic on a refastenable garment, which graphic is not directly visible upon inspection of the interior and exterior surfaces of the garment when the fastening system is engaged in the manner that it would be during use. The hidden graphic may comprise a text message, a pictorial image, or a combination of the two.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven web" means a web of material which is formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use. The outer cover graphic may comprise a text message, a pictorial image, or a combination of the two.

"Permanently bonded" refers to the joining, adhering, connecting, attaching, or the like, of two elements of an absorbent garment such that the elements tend to be and remain bonded during normal use conditions of the absorbent garment.

"Pictorial image" means a graphic consisting of one or more pictures; the terms "text image" and "pictorial image" are mutually exclusive as used herein.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Text message" means a graphic consisting of one or more alphanumeric symbols; the terms "text image" and "pictorial image" are mutually exclusive as used herein.

"Thermoplastic" describes a material that softens when exposed to heat and which substantially returns to a non-softened condition when cooled to room temperature.

These terms may be defined with additional language in the remaining portions of the specification.

BRIEF DESCRIPTION OF THE DRAWINGS

The above-mentioned and other features of the present invention and the manner of attaining them will become more apparent, and the invention itself will be better understood by reference to the following description and the accompanying drawings, wherein similar features in different figures have been given the same reference numeral.

DETAILED DESCRIPTION OF THE DRAWINGS

The principles of the present invention can be incorporated into any suitable disposable absorbent article and its method of manufacture. Examples of such suitable articles include diapers, training pants, swim pants, feminine hygiene products, incontinence products, other personal care or health care garments, or the like. For ease of explanation, the description hereafter will be in terms of a child's training pant.

Figure 1:
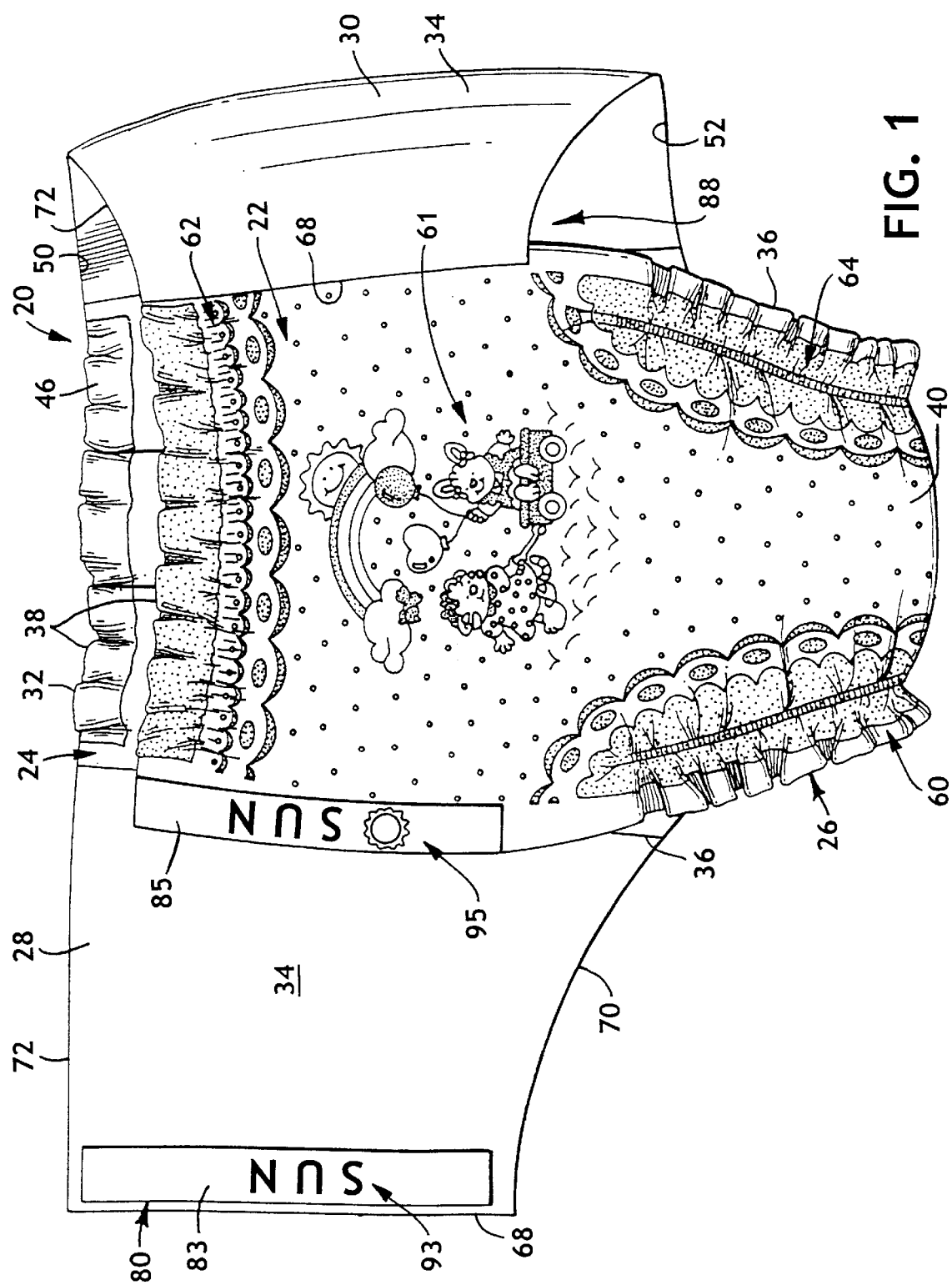
FIG. 1 illustrates a front perspective view of one type of disposable absorbent article incorporating the principles of the present invention, where the fastening system is shown engaged on one side of the absorbent article and disengaged on the other side of the absorbent article.

With reference to FIG. 1, a disposable absorbent article, such as a training pant 20, is illustrated in a partially fastened condition. The training pant 20 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. The illustrated training pant 20 comprises an absorbent chassis 32 and a pair of transversely opposed side panels 34. The absorbent chassis 32 and side panels 34 may be integrally formed or comprise two or more separate elements, as shown.

Figure 2:
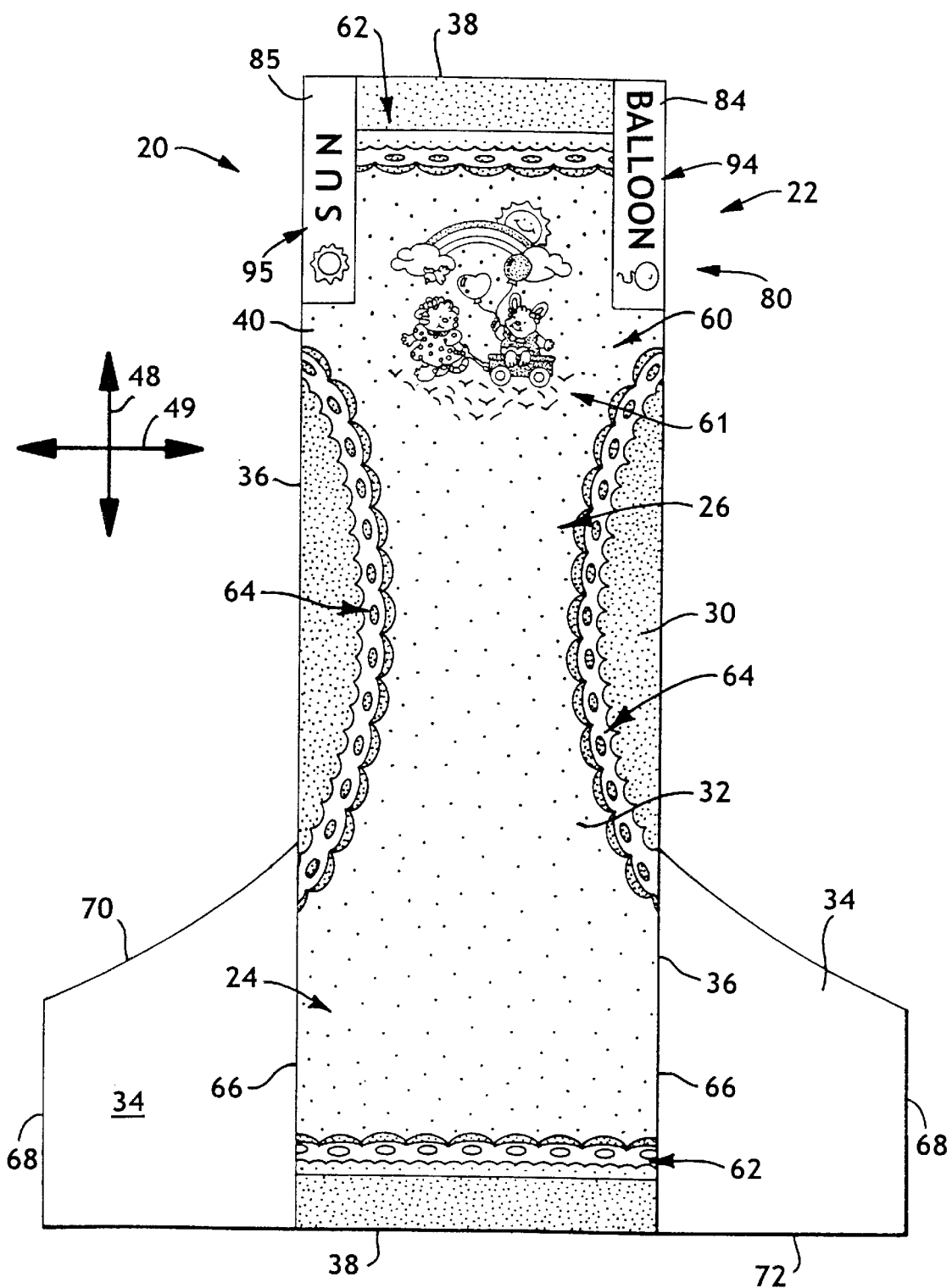
FIG. 2 illustrates a plan view of the disposable absorbent article shown in FIG. 1 in an unfastened, stretched and laid flat condition, and showing the surface of the article that faces away from the wearer.
Figure 3:
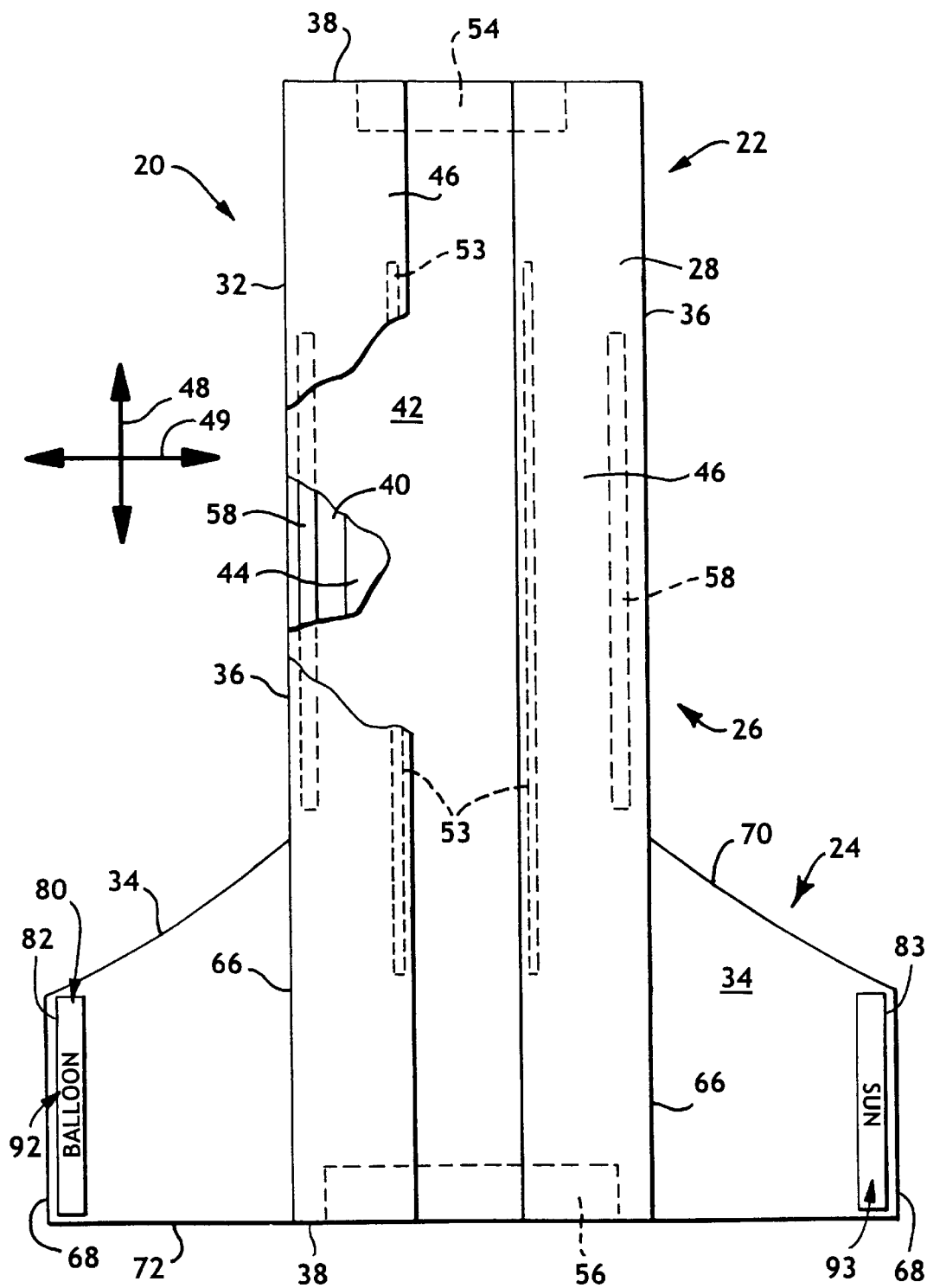
FIG. 3 illustrates a plan view similar to FIG. 2, but showing the surface of the article that faces the wearer when the article is worn, and with portions cut away to show the underlying features.

With additional reference to FIGS. 2 and 3, the absorbent chassis 32 defines a pair of transversely opposed side edges 36 and a pair of longitudinally opposed waist edges 38. The illustrated absorbent chassis 32 comprises an outer cover 40, a bodyside liner 42 (FIG. 3) which is connected to the outer cover in a superposed relation, an absorbent assembly 44 (FIG. 3) which is located between the outer cover and the bodyside liner, and a pair of containment flaps 46 (FIGS. 1 and 3). For reference, arrows 48 and 49 depicting the orientation of the longitudinal axis and the transverse axis, respectively, of the training pant 20 are illustrated in FIGS. 2 and 3.

With the training pant 20 in the fastened position, as partially illustrated in FIG. 1, the front and back waist regions 22 and 24 are joined together to define a three-dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer.

The crotch region 26 of the training pant 20 comprises the portion of the training pant which, when worn, is positioned between the legs of the wearer and covers the lower torso of the wearer. The side panels 34 comprise the portions of the training pant 20 which, when worn, are positioned on the side hip regions of the wearer. The waist edges 38 of the absorbent chassis 32 of the training pant 20 and the side panels 34 are configured to encircle the waist of the wearer when worn and provide the waist opening 50 which defines a waist perimeter dimension. The transversely opposed side edges 36 of the absorbent chassis 32 and the side panels 34 of the training pant 20 generally define the leg openings 52.

The absorbent chassis 32 is configured to contain and/or absorb any body exudates discharged from the wearer. For example, the absorbent chassis 32 desirably although not necessarily comprises the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes a front waist elastic member 54, a rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38, and can extend over part or all of the waist edges. The leg elastic members 58 are desirably operatively joined to the outer cover 40 and/or bodyside liner 42 along the opposite side edges 36 and positioned in the crotch region 26 of the training pant 20.

The flap elastic members 53, the waist elastics 54 and 56, and the leg elastics 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA® and available from E. I. Du Pont de Nemours and Company, Wilmington, Del. U.S.A.

The outer cover 40 desirably comprises a material that is substantially liquid impermeable, and can be elastic, stretchable, or nonstretchable. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis. U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bed-sheets and clothing, as well as the wearer and caregiver. A suitable liquid impermeable film for use as a liquid impermeable inner layer, or a single layer liquid impermeable outer cover 40, is a 1.0 mil polyethylene film commercially available from Edison Plastics Company of South Plainfield, N.J. U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO8044 polyolefin film commercially available from 3M Company, Minneapolis, Minn. U.S.A.

As shown in FIGS. 1 and 2, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered outer cover graphic 60. In this design, the registered graphic 60 includes simulated a primary pictorial image 61, waist ruffles 62, and simulated leg ruffles 64. The primary pictorial image 61 includes a rainbow, sun, clouds, animal characters, wagon and balloons. Any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. No. 5,766,389 issued Jun. 16, 1998 to Brandon et al., which are incorporated herein by reference. The primary pictorial image 61 is desirably positioned in the front waist region 22 along the longitudinal centerline of the training pant 20.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner may be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent assembly 44 (FIG. 3) is positioned between the outer cover 40 and the bodyside liner 42, which components can be joined together by any suitable means such as adhesives as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulosic fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich. U.S.A. and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and comprises a blend of wood pulp fluff and superabsorbent material. One preferred type of fluff is identified with the trade designation CR1654, available from Kimberly-Clark Corporation, Neenah, Wis. U.S.A., and is a bleached, highly absorbent sulfate wood pulp containing primarily soft wood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that maintains the integrity and/or shape of absorbent assembly.

The absorbent chassis 32 can also incorporate other materials that are designed primarily to receive, temporarily store, and/or transport liquid along the mutually facing surface with absorbent assembly 44, thereby maximizing the absorbent capacity of absorbent assembly. One suitable material is referred to as a surge layer (not shown) and comprises a material having a basis weight of about 50 grams per square meter, and comprising a through-air-bonded-carded web of a homogenous blend of 60 percent 3 denier bicomponent fiber comprising a polyester core/polyethylene sheath, commercially available from BASF Corporation, and 40 percent 6 denier polyester fiber, commercially available from Hoechst Celanese Corporation, Portsmouth, Vir. U.S.A.

As noted previously, the illustrated training pant 20 has a side panel 34 disposed on each side of the absorbent chassis 32. The pair of transversely opposed side panels 34 are permanently bonded to the absorbent chassis 32 in at least one of the waist regions 22 and 24 and releasably attached to the absorbent chassis in the opposite waist region. For example, as shown best in FIGS. 2 and 3, the side panels 34 are permanently bonded to and extend transversely beyond the side edges 36 of the chassis in the back waist region 24 along an attachment line 66. It is desirable but not necessary for the side panels 34 to extend transversely outward from the side edges 36 of the absorbent chassis 32. Moreover, the side panels can be formed as a portion of a component of the composite structure 33, such as the outer cover or the bodyside liner.

The illustrated side panels 34 define a distal edge 68 spaced from the attachment line 66 and inner and outer edges 70 and 72 that extend from the side edges 36 of the absorbent chassis 32 to the distal edges. The inner edges 70 of the side panels 34 are desirably although not necessarily angled relative to the transverse axis 49 to provide greater coverage toward the back of the pant as compared to the front of the pant. The outer edges 72 are desirably parallel to and aligned with the back waist edge 38 of the absorbent chassis 32. The side panels 34 can have an average length dimension measured parallel to the longitudinal axis 48 that is about 20 percent or greater, and particularly about 25 percent or greater, of the overall length dimension of the absorbent article, also measured parallel to the longitudinal axis 48.

The side panels 34 can be permanently bonded to the absorbent chassis 32 along the attachment line 66 using attachment means known to those skilled in the art such as adhesive, thermal or ultrasonic bonding. In such a configuration, each of the side panels 34 can be releasably attached to the absorbent chassis 32 in the front waist region 22 of the training pant 20 as will be discussed hereinafter in more detail. Alternatively, the side panels 34 can be permanently bonded to the side edges 36 in the front waist region 22 and releasably attached to the side edges 36 in the back waist region 24 if it is desired that the fasteners be located towards the back of the wearer. Such a configuration may be desirable to prevent a wearer from unfastening the article prematurely.

Each of the side panels 34 can include one or more individual, distinct pieces of material. In particular embodiments, for example, each side panel 34 can include front and back side panel portions that are joined at a seam (not shown). Still alternatively, each individual side panel 34 can include a single piece of material which is folded over upon itself along an intermediate fold line (not shown).

The side panels 34 desirably comprise an elastic material capable of stretching in a direction generally parallel to the transverse axis 49 of the training pant 20. Suitable elastic materials, as well as one described process of incorporating elastic side panels into a training pant, are described in the following U.S. Pat. Nos.: 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. In particular embodiments, the elastic material comprises a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Mormon; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or bodyside liner 42.

The training pant 20 according to the present invention also includes a fastening system 80 for securing the training pant about the waist of the wearer (FIGS. 2 and 3). The illustrated fastening system 80 includes a pair of fastening components designated first and second fastening components 82 and 83 that are adapted to refastenably connect to a pair of mating fastening components designated first and second mating fastening components 84 and 85. As illustrated, the first fastening component 82 and the first mating fastening component 84 are on the wearer's left-hand side of the training pant 20 and are designed to releasably engage one another, and the second fastening component 83 and the second mating fastening component 85 are on the wearer's righthand side of the training pant and are designed to releasably engage one another. In one embodiment, one surface of each of the first and second fastening components 82 and 83 comprises a plurality of engaging elements that project from that surface. The engaging elements of these fastening components 82 and 83 are adapted to repeatedly engage and disengage the engaging elements of the mating fastening components 84 and 85.

In one particular embodiment, the first and second fastening components 82 and 83 each comprise hook type fasteners and the first and second mating fastening components 84 and 85 each comprise complementary loop type fasteners. In another particular embodiment, the first and second fastening components 82 and 83 each comprise loop type fasteners and the first and second mating fastening components 84 and 85 each comprise complementary hook type fasteners. Loop type fasteners typically comprise a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically comprise a fabric or material having a base or backing structure and a plurality of hook members extending upwardly from at least one surface of the backing structure. In contrast to the loop type fasteners which desirably comprise a flexible fabric, the hook material advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82 and 83 or the mating fastening components 84 and 85 are available from Velcro Industries B.V., Amsterdam, Netherlands or affiliates thereof, and are identified as Velcro HTH-829 with a uni-directional hook pattern and having a thickness of about 0.089 millimeters (3.5 mils) and HTH-851 with a uni-directional hook pattern and having a thickness of about 0.051 millimeters (2 mils).

With reference to FIG. 3, the first and second fastening components 82 and 83 are desirably but not necessarily located on the inner surface 28 of the training pant 20 in the back waist region 24. The first and second fastening components 82 and 83 are desirably positioned along the distal edges 68 of the side panels 34. The first and second fastening components 82 and 83 may be adhered to the side panels 34 by any means known to those skilled in the art such as adhesive bonds, sonic bonds or thermal bonds.

With reference to FIG. 2, the first and second mating fastening components 84 and 85 are located on the outer surface 30 of the training pant 20 in the front waist region 22. The first and second mating fastening components 84 and 85 are sized to receive the first and second fastening components 82 and 83 and are desirably positioned along the side edges 36 of the absorbent chassis 32 abutting the front waist edge 38. The first and second mating fastening components 84 and 85 may be adhered to the outer cover 40 by any means known to those skilled in the art such as adhesive bonds, sonic bonds or thermal bonds. In an alternative embodiment, the training pant 20 includes only a single mating fastening component disposed in the front waist region 22 for refastenably connecting the first and second fastening components 82 and 83 (not shown). In a further alternative embodiment, the outer cover 40 functions as a mating fastening component in that it comprises a material that is releasably engageable with the first and second fastening components 82 and 83. The first and second mating fastening components 84 and 85 are desirably rectangular, although they may alternatively be square, round, oval, curved or otherwise nonrectangularly shaped.

When the fastening components and mating fastening components 82–85 are releasably engaged, the side edges 36 of the absorbent chassis 32 and the inner edges 70 of the side panels 34 define the leg openings 52, and the waist edges 38 of the absorbent chassis and the outer edges 72 of the side panels define the waist opening 50. The fastening components and mating fastening components 82–85 may be releasably secured together to form refastenable seams 88, as illustrated at the wearer's left-hand side in FIG. 1.

The first and second fastening components 82 and 83 each define a length dimension aligned generally parallel with the longitudinal axis 48 of the training pant 20 and a width dimension aligned generally parallel with the transverse axis 49 of the training pant. For a child of about 9 to about 15 kilograms (20–30 pounds), for example, the length dimension of the first and second fastening components 82 and 83 is desirably from about 5 to about 13 centimeters, such as about 10 centimeters, and the width dimension is desirably from about 0.5 to about 3 centimeters, such as about 1 centimeter. The first and second fastening components 82 and 83 desirably have a length-to-width ratio of about 2 or greater, such as about 2 to about 26, and particularly about 5 or greater, such as about 5 to about 8.

To enhance the toilet training process, the training pant 20 can include additional graphics located directly on the fastening components and the mating fastening components 82–85. Because these graphics are desirably located directly on the fastening components and the mating fastening components 82–85, they are hidden from view when the fasteners are engaged and thus form hidden graphics. The hidden graphics are not directly visible from either the inner surface 28 or the outer surface 30 of the garment 20 when the fasteners 82–85 are engaged.

As shown in FIGS. 1–3, both the fastening components 82 and 83 and the mating fastening components 84 and 85 may include graphics disposed directly on their attachment surfaces. In the illustrated embodiment, the first fastening component 82 has a graphic 92 directly on its releasable attachment surface. This graphic 92 is in the form of a text message of the word "BALLOON". The second fastening component 83 has a graphic 93 directly on its releasable attachment surface, and this graphic 93 is in the form of a text message of the word "SUN". The first and second mating fastening components 84 and 85 also include graphics 94 and 95, respectively, that are disposed directly on their releasable attachment surfaces. The graphic 94 on the first mating fastening component 84 includes both a text message of the word "BALLOON" and also a pictorial image representing a balloon. The graphic 95 on the second mating fastening component 85 includes both a text message of the word "SUN" and also a pictorial image representing a sun.

Incorporation of a graphic on at least one of the first fastening component 82 and the first mating fastening component 84 causes the refastenable seam 88 on the wearer's left-hand side of the training pant 20 to include a hidden graphic. Similarly, the incorporation of a graphic on at least one of the second fastening component 83 and the second mating fastening component 85 causes the refastenable seam 88 on the wearer's right-hand side to include a hidden graphic.

Desirably, the graphics on the engaging fastening elements may be related in subject matter. As best shown in FIG. 1, for instance, the graphics 93 and 95 on the second fastening component 83 and the second mating fastening component 85 have a subject matter relationship. Both graphics 93 and 95 include the identical word "SUN" and one of the graphics 95 includes a pictorial image representing a sun. A similar situation exists with the graphics 92 and 94 on the first fastening component 82 and the first mating fastening component 84 involving a balloon. These graphics provide many interaction and education opportunities for the child and the caregiver.

A further opportunity for interaction and education exists when the hidden graphics are related in subject matter to the outer cover graphics. In the illustrated embodiment, each of the graphics 92–95 that form part of the hidden graphics are related in subject matter to the primary pictorial image 61 of the outer cover graphics 60.

Figure 4:
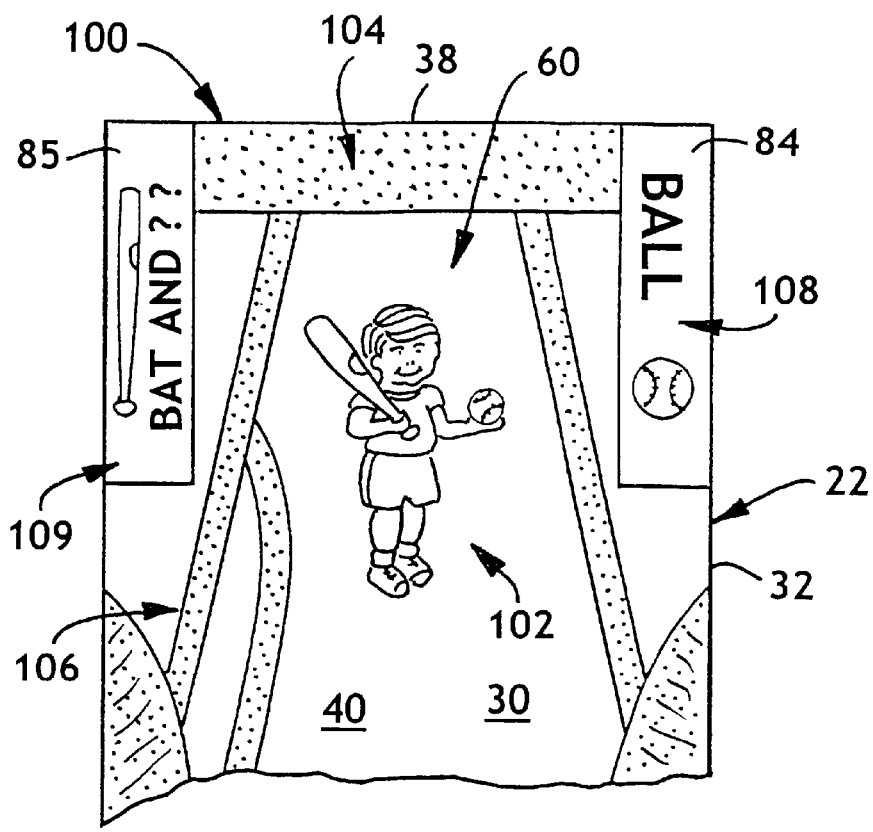
FIG. 4 illustrates a front perspective view of a front waist region of an alternative disposable absorbent article incorporating the principles of the present invention.

Another illustrative embodiment of a training pant 100 designed for use by young boys and including hidden graphics is shown in FIG. 4. The front perspective view of the a front waist region 22 of the training pant 100 shows a registered outer cover graphic 60 including a primary pictorial image 102, waistband highlighting 104, and a simulated "fly opening" 106 typical of a boy's underwear. The primary pictorial image 102 includes a character, a bat and a ball. The graphics 108 and 109 disposed directly on the first and second mating fastening components 84 and 84, respectively, are related in subject matter to the outer cover graphics 60, and in particular to the primary pictorial image 102. Moreover, the graphics 108 and 109 are related in subject matter to each other, and specifically, each graphic refers to one and the other of two items that are commonly associated with one another, here "bat" and "ball," and together the graphics jointly present a question and answer. Of course, the outer cover graphics and the hidden graphics can be any type of desired text message or pictorial image.

Figure 5:
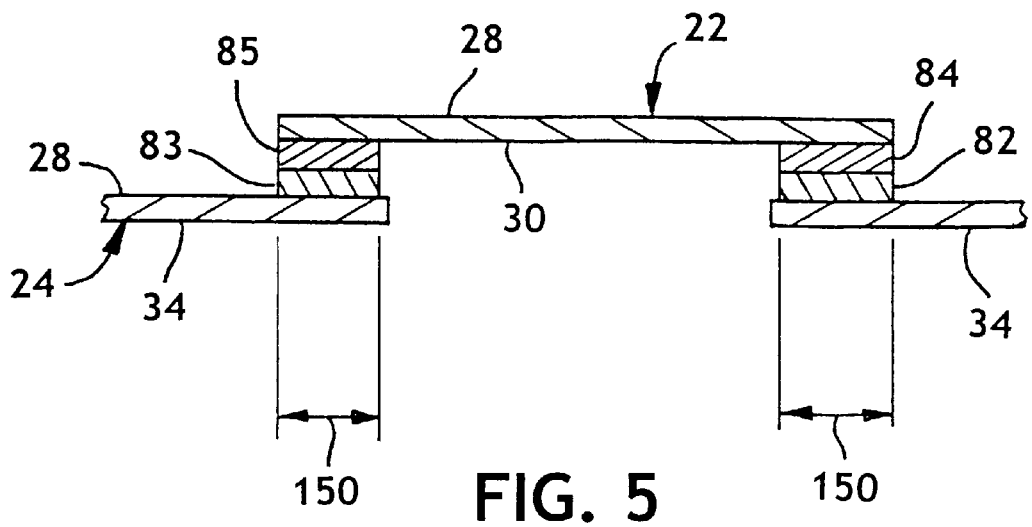
FIG. 5 schematically illustrates in section a back waist region overlapping the front waist region of FIG. 4 with the fastening components and mating fastening components releasably engaged.

FIG. 5 illustrates schematically the overlap of the back waist region 24 and the front waist region 22. With the fastening components 82 and 83 releasably engaged with the mating fastening components 84 and 85, an overlap region is formed which represents the portions of the front and back waist regions 22 and 24 that overlap and face one another. As shown in FIG. 5, the overlap region in this particular embodiment consists essentially of the combined width of the engaged fastening components 82 and 84 and the engaged fastening components 83 and 85, over the combined lengths of these fastening components 82–85. These regions which jointly form the overlap region are depicted by arrows 150. The graphics 108 and 109 are disposed in the overlap region 150 and thus form hidden graphics.

Figure 6:
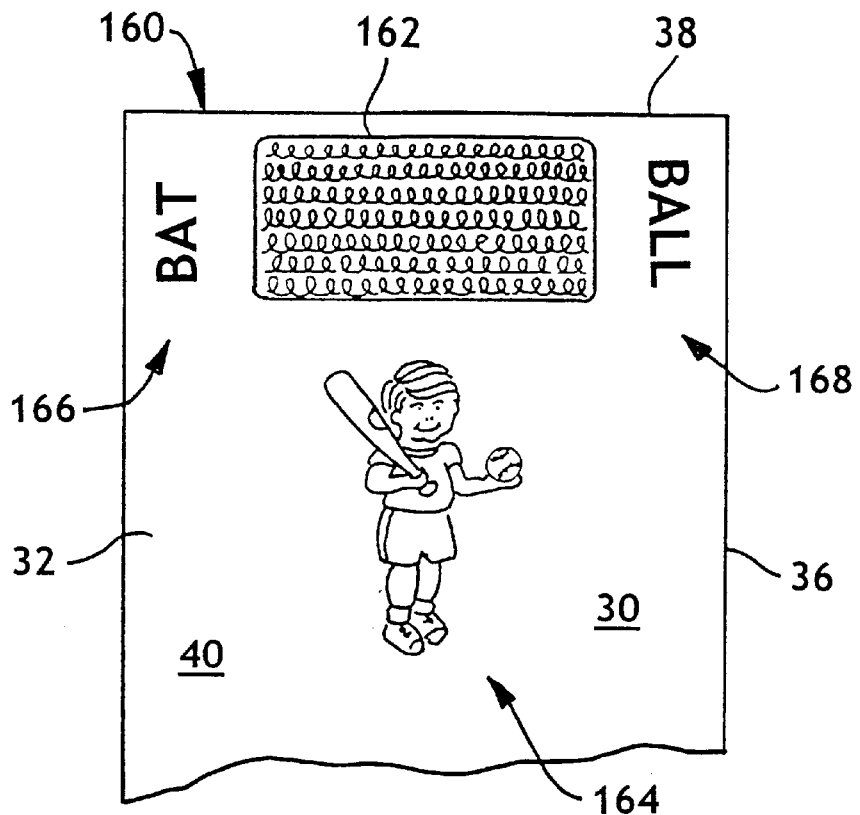
FIG. 6 illustrates a front perspective view of a front waist region of another alternative disposable absorbent article incorporating the principles of the present invention.

Another illustrative embodiment of a front waist region 22 of a training pant 160 including hidden graphics is shown in FIG. 6. A single mating fastening component 162 comprising a separate mechanical fastening element is centrally positioned on and bonded to the outer cover 40 in the front waist region 22. An outer cover graphic 164 is disposed on the outer cover longitudinally inward of the mating fastening component 162. The training pant 160 also includes a pair of graphics 166 and 168 that are related in subject matter to the outer cover graphic 164 and related in subject matter to each other. The graphics 166 and 168 in this embodiment are disposed on the outer surface 30 of the outer cover 40 and located transversely outward from the mating fastening component 162.

Figure 7:
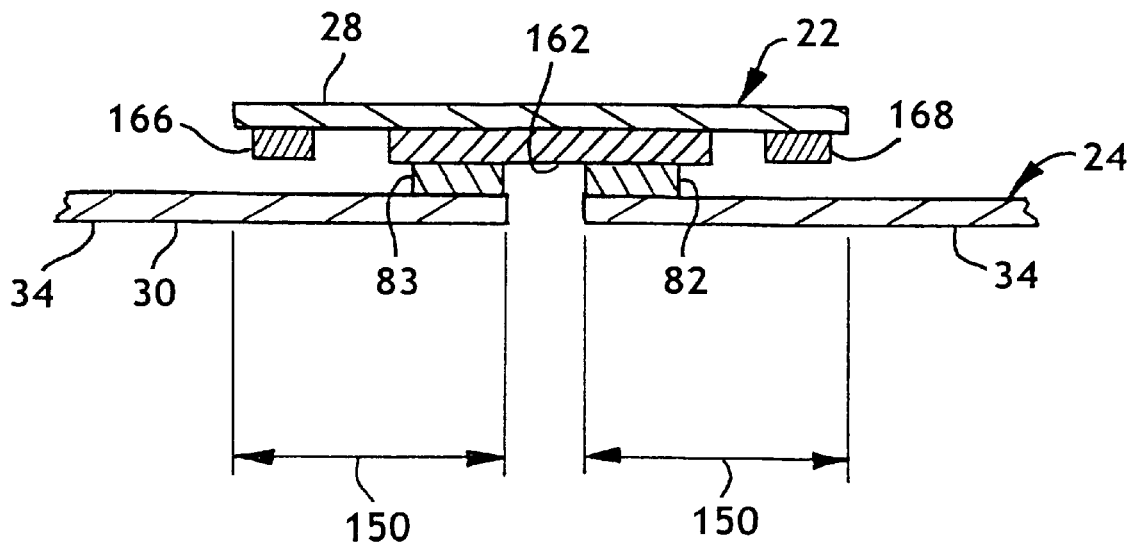
FIG. 7 schematically illustrates in section a back waist region overlapping the front waist region of FIG. 6 with the fastening components and mating fastening component releasably engaged.

The training pant 160 is shown in FIG. 7 with the back waist region 24 overlapping the front waist region 22. With the fastening components 82 and 83 releasably engaged with the mating fastening component 162, a relatively large overlap region 150 is formed. The overlap region 150 not only includes the overlapping portions of the fastening components 82, 83 and 162, but also portions transversely outward from the fastening components 82 and 83 to the side edges 36 of the absorbent chassis 32. To illustrate their position, the graphics 166 and 168 are shown as projecting from the outer surface 30 of the front waist region 22. The graphics 166 and 168 are disposed in the overlap region 150 and form hidden graphics.

Figure 8:
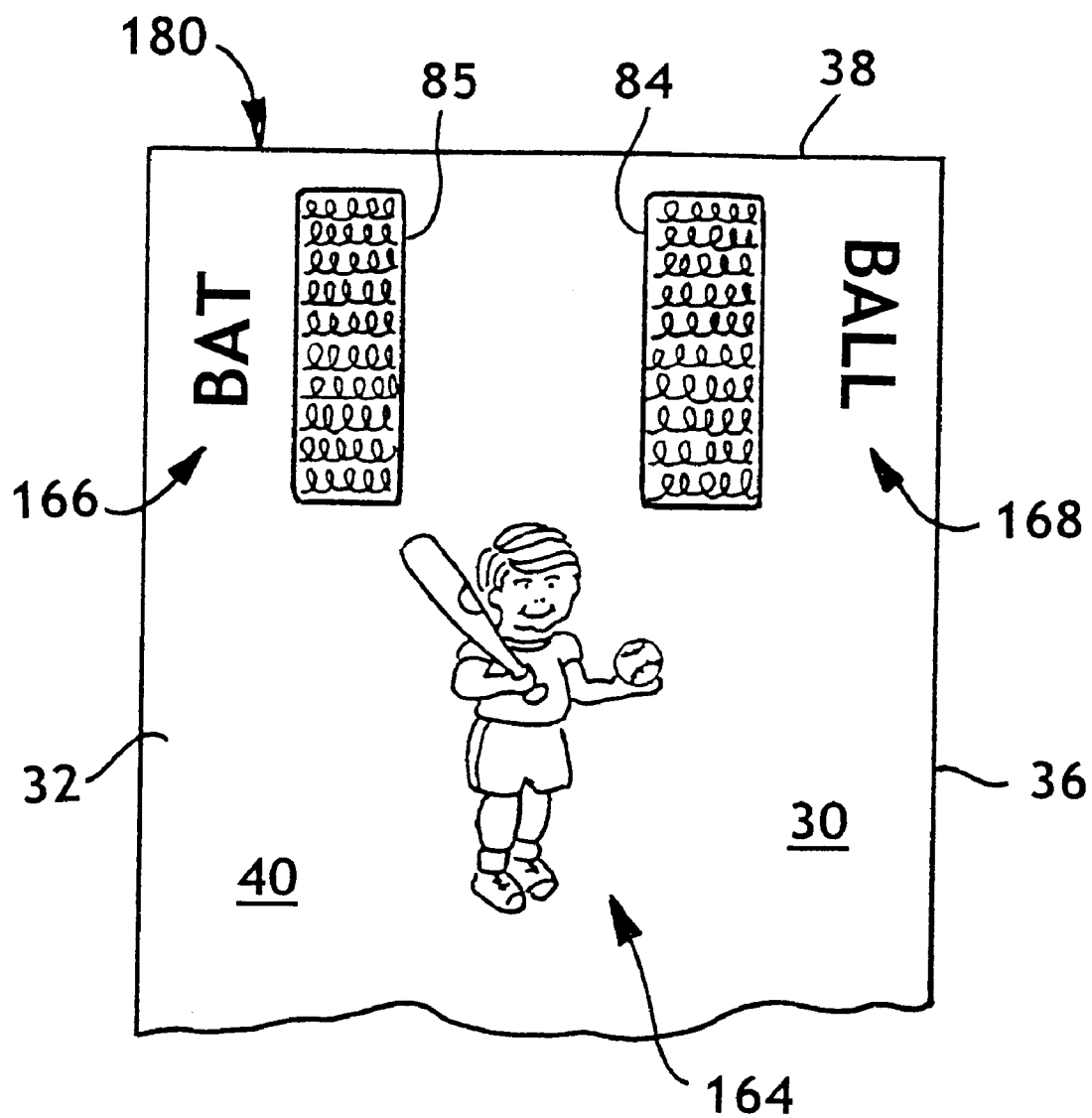
FIG. 8 illustrates a front perspective view of a front waist region similar to FIG. 6 but illustrated with a pair of mating fastening components.

The training pant 180 illustrated in FIG. 8 is similar to the training pant 160 shown in FIG. 6. The training pant 180 of FIG. 8, however, includes first and second mating fastening components 84 and 85 bonded to the outer cover 40 in the front waist region 22. Graphics 166 and 168 of the training pant 180 are located transversely outward from the mating fastening components 84 and 85. When the fastening components 82 and 83 are releasably attached to the mating fastening components 84 and 85, the graphics 166 and 168 are positioned in the overlap region 150 and form hidden graphics.

Figure 9:
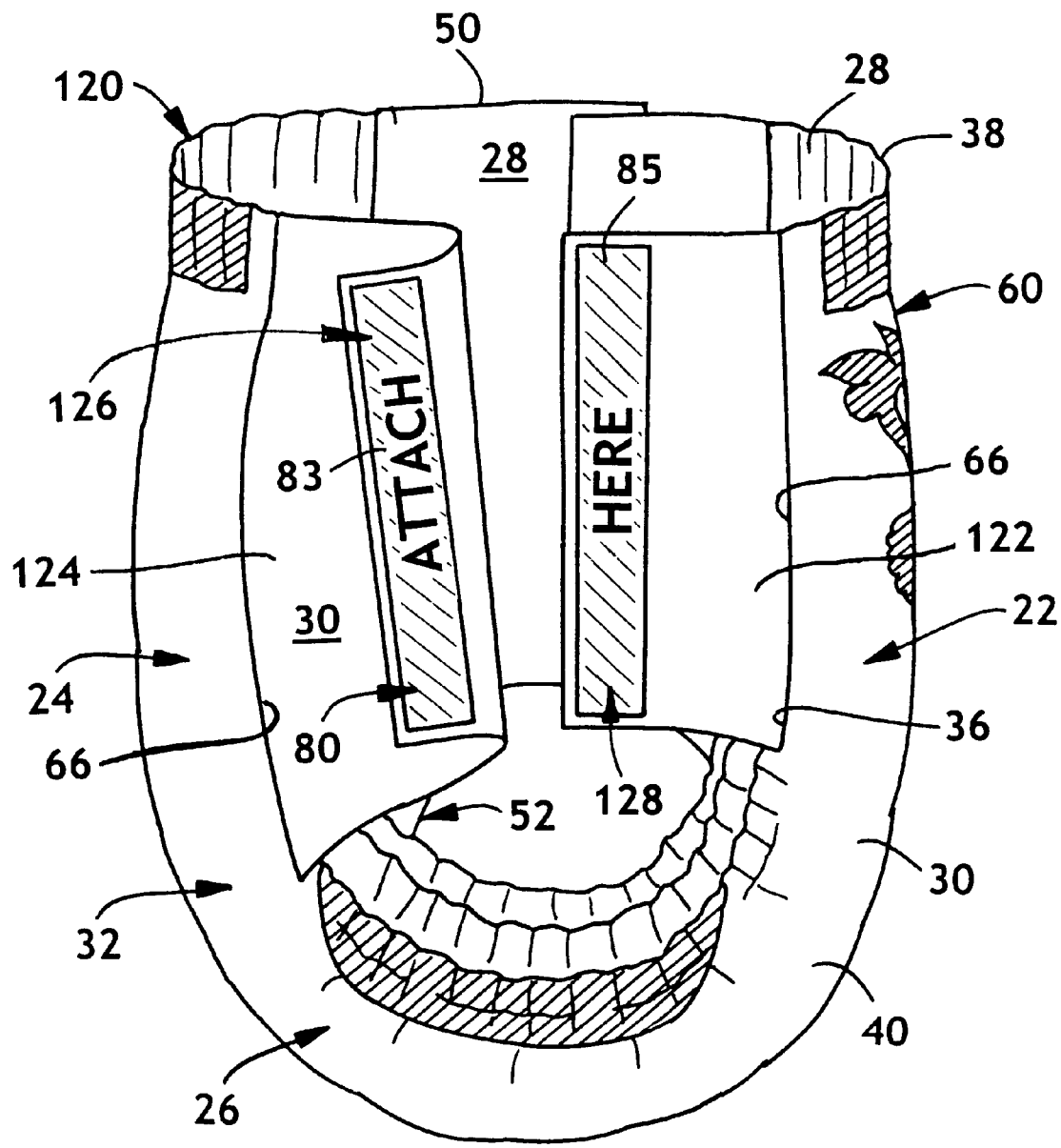
FIG. 9 illustrates a side view of another alternative disposable absorbent article incorporating the principles of the present invention.

A further illustrative embodiment of a training pant 120 including hidden graphics is shown in FIG. 9, which depicts the wearer's right-hand side of the training pant. In this embodiment, the training pant 120 includes side panels 122 attached to opposite sides of the absorbent chassis 32 in the front waist region 22 and side panels 124 attached to opposite sides of the absorbent chassis in the back waist region 24. The side panels 122 and 124 may be attached to the absorbent chassis 32 at attachment lines 66, and desirably comprise elastic materials that stretch in a direction parallel to the transverse axis of the training pant 120.

The training pant 120 includes first and second fastening components 82 and 83 attached to the side panels 124 in the back waist region 24 and first and second mating fastening components 84 and 85 attached to the side panels 122 in the front waist region 22. As illustrated, the graphics 126 on the first and second fastening components 82 and 83 desirably comprise both a text message and a pictorial image to facilitate fastening and refastening of the fastening system. Likewise, the graphics 128 on the first and second mating fastening components 84 and 85 desirably comprise both a text message and a pictorial image related to the graphics 126 on first and second fastening components 82 and 83. It is useful for the first and second fastening components 82 and 83 and the first and second mating fastening components 84 and 85 to include identical or similar pictorial images, such as parallel diagonal lines, that denote proper attachment zones. Suitable pictorial images include, for instance, matching patterns, lines, shapes, or the like, which desirably are dissimilar and easily distinguishable from the outer cover graphics. The graphics 126 can also be related in subject matter to the outer cover graphic.

Figure 10:
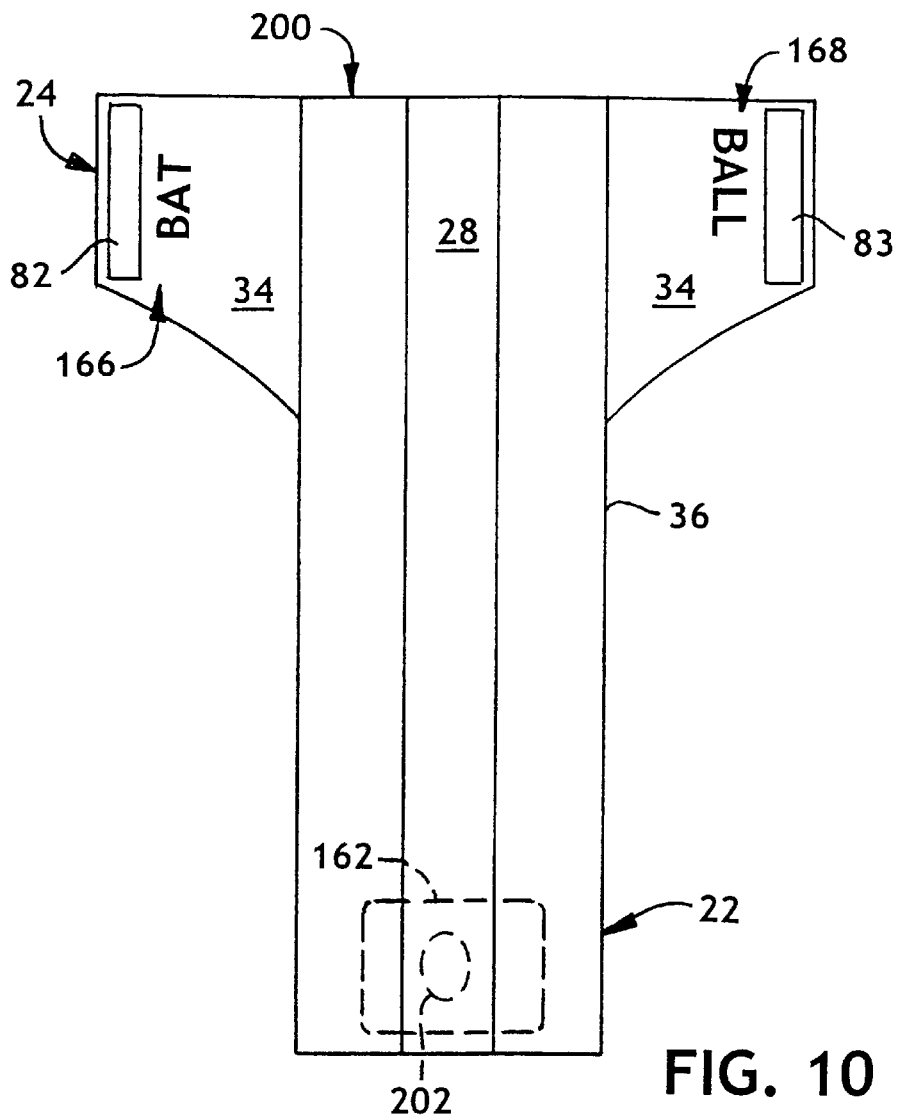
FIG. 10 illustrates a plan view similar to FIG. 3 of a further alternative disposable absorbent article incorporating the principles of the present invention, showing the surface of the article that faces the wearer when the article is worn.

A further embodiment of a training pant 200 is illustrated in FIG. 10, from the perspective of the inner surface 28. The training pant 200 includes first and second fastening components 82 and 83 bonded to the inner surface 28 of each side panel 34 in the back waist region 24. The training pant 200 also includes a mating fastening component 162 bonded to the outer surface 30 in the front waist region 22. With the back waist region 24 overlapping the front waist region 22, the fastening components 82 and 83 can releasably engage the mating fastening component 162. With additional reference to FIG. 11, the overlapping waist regions 22 and 24 form an overlap region 150.

Figure 11:
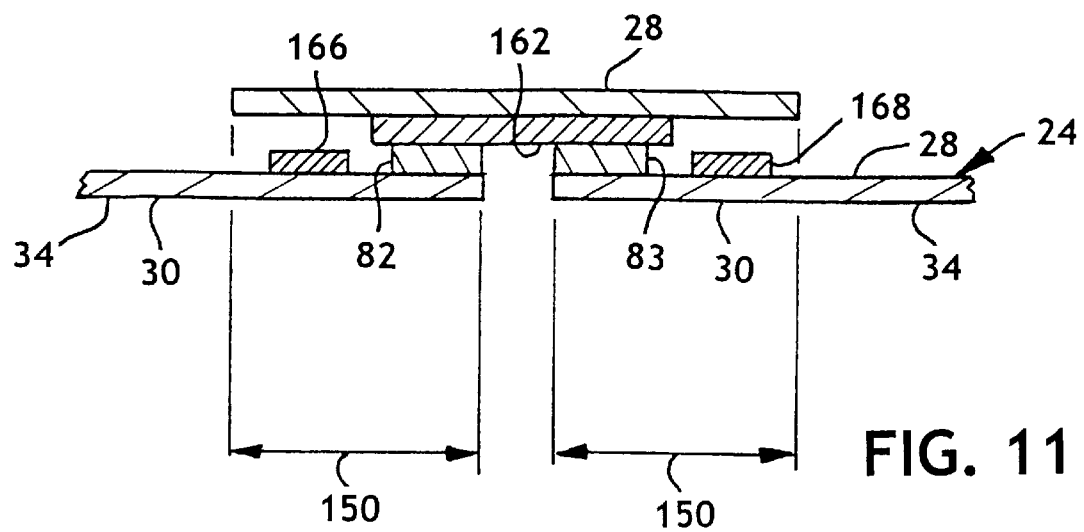
FIG. 11 schematically illustrates in section the back waist region overlapping the front waist region of FIG. 10 with the fastening components and mating fastening component releasably engaged.

The training pant 200 also includes a graphic 202 disposed on the mating fastening component 162 in the front waist region 22 and graphics 166 and 168 disposed on the side panels 34 in the back waist region 24. The graphics 166 and 168 are positioned transversely inward from and in close proximity to the respective first and second fastening components 82 and 83. As shown in FIG. 11, the graphics 166 and 168 are completely disposed within the overlap region 150 when the fasteners are engaged and form hidden graphics.

The training pants may further include releasable side bonds (not shown) for improved reliability of maintaining the pant in a prefastened condition particularly when it is being pulled on or off over the hips of the wearer. Such releasable side bonds are desirably configured to be readily broken such that the caregiver can easily remove the training pant after it has been soiled. The releasable side bonds desirably comprise ultrasonic point bonds. Absorbent articles including such releasable side bonds are further described in U.S. patent application Ser. No. 09/100,574 titled "Disposable Absorbent Articles Having Passive Side Bonds And Adjustable Fastening Systems" filed Jun. 19, 1998 by Elsberg, which is incorporated herein by reference.

Figure 12:
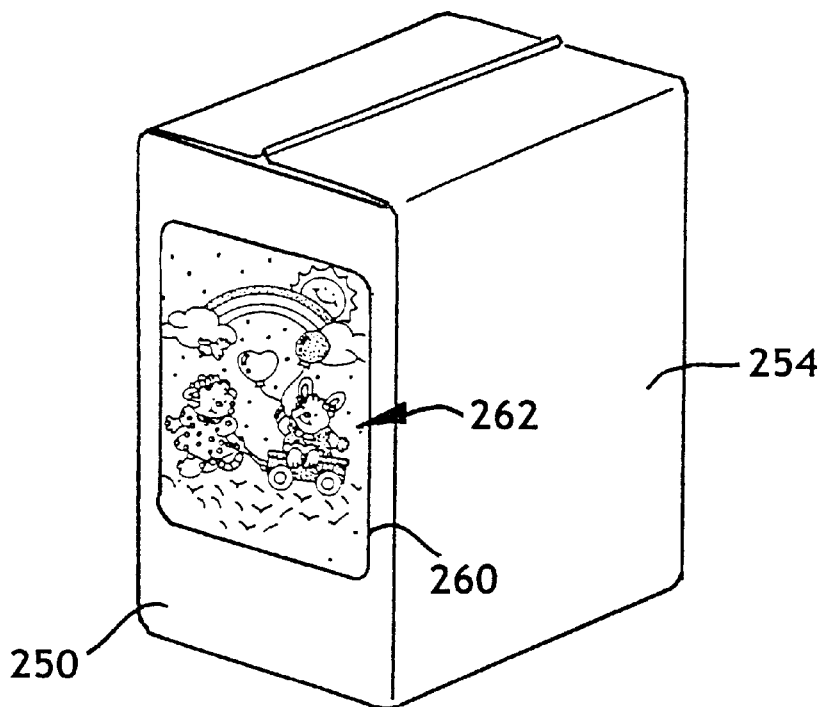
FIG. 12 illustrates a package of prefastened absorbent articles with hidden graphics.
Figure 13:
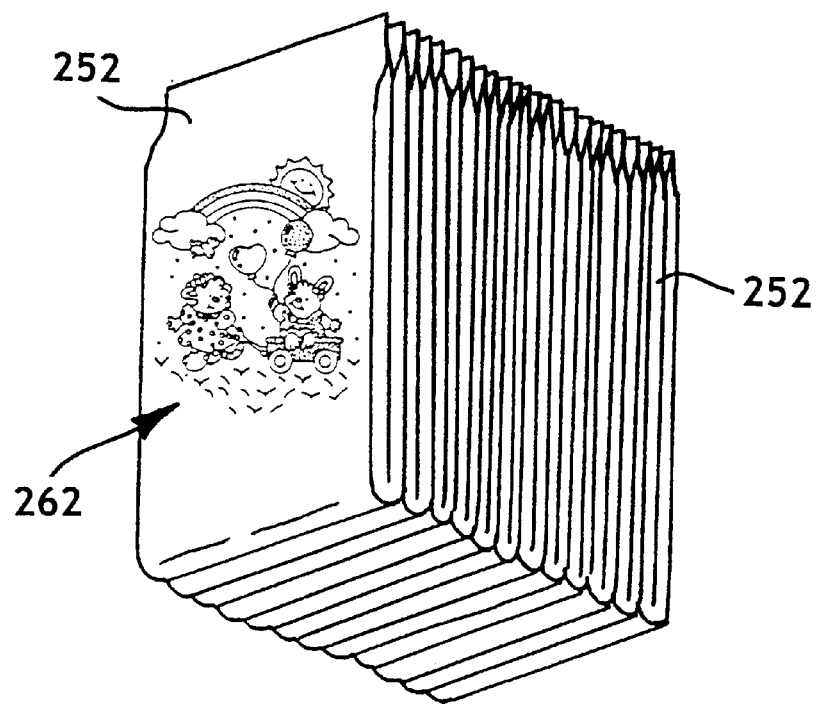
FIG. 13 illustrates a plurality of prefastened absorbent articles that are prepared for insertion into a bag.

A package 250 of prefastened absorbent articles with hidden graphics is illustrated in FIG. 12. The package 250 includes a plurality of prefastened absorbent articles 252 disposed within a sealed bag 254. The bag 254 defines an interior space to receive the absorbent articles 252. The bag 254 can but need not include a window 260 for viewing the absorbent articles 252, and in particular the outer cover graphic 262. FIG. 13 illustrates a plurality of absorbent articles 252 that are prefastened and prepared for insertion into the bag 254.

The methods of the different aspects of the present invention are directed at reliably and consistently providing the refastenable training pant 20 as described herein and representatively illustrated in the Figures. The various components of the training pant 20 are integrally assembled together employing various types of suitable attachment means, such as adhesive, sonic and thermal bonds or combinations thereof. The graphics may be formed on the fastening components and the mating fastening components by any suitable method, including but not limited to printing, such as flexographic, rotogravure, or inkjet; assembling a multiple layer composite with at least one of the layers containing the graphics; or the like.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A package of absorbent articles with hidden graphics, comprising:

a bag defining an interior space; and a plurality of prefastened absorbent articles disposed within the interior space, the prefastened absorbent articles each defining first and second longitudinally spaced waist regions and a crotch region which extends between and interconnects the waist regions, the absorbent articles each comprising:

fastening components disposed in the first waist region;

at least one mating fastening component disposed in the second waist region, the first and second waist regions overlapping one another to define an overlap region, and the fastening components releasably engaged with the at least one mating fastening component; and a graphic disposed in the overlap region to define a hidden graphic.

2. The package of claim 1, wherein the first waist region overlaps the second waist region, and the hidden graphic is disposed on an inner surface of the first waist region.

3. The package of claim 2, wherein the hidden graphic is disposed on a fastening component.

4. The package of claim 1, wherein the hidden graphic is disposed in close proximity to and transversely inward from a fastening component.

5. The package of claim 1, wherein the absorbent articles each define inner and outer surfaces and opposite side panels in the first waist region, and both the fastening components and hidden graphics are disposed on inner surfaces of the opposite side panels.

6. The package of claim 1, wherein the first waist region overlaps the second waist region, and the hidden graphic is disposed on an outer surface of the second waist region.

7. The package of claim 6, wherein the hidden graphic is disposed on a mating fastening component.

8. The package of claim 6, wherein the hidden graphic is disposed in close proximity to and transversely outward from a mating fastening component.

9. The package of claim 1, wherein: the absorbent articles each define inner and outer surfaces; the at least one mating fastening component comprises separate elements bonded to the outer surface; and hidden graphics are disposed on the outer surface transversely outward from the separate elements.

10. The package of claim 1, further comprising an outer cover graphic that is visible on an outer surface of the prefastened absorbent articles.

11. The package of claim 10, wherein the outer cover graphic is related in subject matter to the hidden graphic.

12. The package of claim 11, wherein the outer cover graphic comprises a pictorial image and the hidden graphic comprises a text message.

13. The package of claim 11, wherein the outer cover graphic and hidden graphic each comprise text messages that refer to one and the other respectively of two items that are commonly associated with one another.

14. The package of claim 11, wherein the outer cover graphic and hidden graphic each comprise text messages that jointly form a sentence, thought or action.

15. The package of claim 11, wherein the outer cover graphic and hidden graphic each comprise pictorial images that illustrate different sizes, shapes, colors of a common object.

16. The package of claim 11, wherein the outer cover graphic and hidden graphic each comprise pictorial images that illustrate one and the other respectively of two objects that are commonly associated with one another.

17. The package of claim 11, wherein the outer cover graphic and hidden graphic each comprise pictorial images that illustrate respectively geometrically mating or engaging elements.

18. The package of claim 1, wherein the fastening components and the mating fastening components comprise mechanical fastening elements.

19. An absorbent article, comprising:

an absorbent chassis defining a longitudinal axis, a transverse axis, an inner surface, an opposite outer surface, first and second longitudinally spaced waist regions, and a crotch region which extends between and interconnects the first and second waist regions, the first waist region defining a pair of transversely opposed side panels;

first and second fastening components disposed respectively on the pair of side panels;

at least one mating fastening component disposed in the second waist region, the fastening components adapted to releasably engage the at least one mating fastening component; and a graphic disposed on the absorbent chassis;

wherein attachment of the fastening components to the at least one mating fastening component forms an overlap region of the first and second waist regions, the graphic being disposed in the overlap region and in the second waist region, separate from and transversely outward from the at least one mating fastening component, to define a hidden graphic.

20. The absorbent article of claim 19, further comprising a pair of mating fastening components disposed in the second waist region, the graphic being separate from and transversely outward from the mating fastening components.

21. The absorbent article of claim 19, further comprising an outer cover graphic that is related in subject matter to the hidden graphic.

22. The absorbent article of claim 21, wherein the outer cover graphic comprises a pictorial image and the hidden graphic comprises a text message.

23. The absorbent article of claim 21, wherein the outer cover graphic and hidden graphic each comprise pictorial images.

24. The absorbent article of claim 23, wherein pictorial images illustrate one and the other respectively of two objects that are commonly associated with one another.

25. The absorbent article of claim 19, wherein the hidden graphics comprise freeform graphics.

26. The absorbent article of claim 19, wherein the hidden graphic is not symmetrical relative to a longitudinal axis.

27. A package containing a plurality of absorbent articles according to claim 19, the absorbent articles being in a prefastened condition wherein the first and second fastening components are releasably attached to the at least one mating fastening component and the graphic forms a hidden graphic.

28. An absorbent article, comprising:

an absorbent chassis defining a longitudinal axis, a transverse axis, an inner surface, an opposite outer surface, first and second longitudinally spaced waist regions, and a crotch region which extends between and interconnects the first and second waist regions, the first waist region defining a pair of transversely opposed side panels;

first and second fastening components disposed respectively on the pair of side panels and comprising mechanical fastening elements;

at least one mating fastening component disposed in the second waist region and comprising mechanical fastening elements, the fastening components adapted to releasably engage the at least one mating fastening component; and a graphic disposed on the absorbent chassis;

wherein attachment of the fastening components to the at least one mating fastening component forms an overlap region of the first and second waist regions, the graphic being disposed in the overlap region and on the inner surface of one of the side panels to define a hidden graphic.

29. The absorbent article of claim 28, wherein the graphic is disposed on one of the first and second fastening components.

30. The absorbent article of claim 28, wherein the graphic is disposed in close proximity to and transversely inward from one of the fastening components.

31. The absorbent article of claim 28, further comprising an outer cover graphic that is related in subject matter to the hidden graphic.

32. The absorbent article of claim 31, wherein the outer cover graphic comprises a pictorial image and the hidden graphic comprises a text message.

33. The absorbent article of claim 31, wherein the outer cover graphic and hidden graphic each comprise pictorial images.

34. The absorbent article of claim 33, wherein pictorial images illustrate one and the other respectively of two objects that are commonly associated with one another.

35. The absorbent article of claim 28, wherein the side panels are elastomeric in a direction generally parallel to the transverse axis.

36. A package containing a plurality of absorbent articles according to claim 28, the absorbent articles being in a prefastened condition wherein the first and second fastening components are releasably attached to the at least one mating fastening component and the graphic forms a hidden graphic.

37. An absorbent article defining a longitudinal axis, a transverse axis, first and second longitudinally spaced waist regions, and a crotch region which extends between and interconnects the first and second waist regions, the absorbent article comprising a fastening system that comprises first and second fastening components disposed in the first waist region and first and second mating fastening components disposed in the second waist region, at least one of the mating fastening components comprising a freeform graphic, the first and second fastening components being substantially the same size or larger than the freeform graphic and being substantially the same size or larger than the first and second mating fastening components such that the freeform graphic forms a hidden graphic when the first and second fastening components are centrally positioned relative to and engaged with the first and second mating fastening components.

38. The absorbent article of claim 31, wherein the fastening components and the mating fastening components comprise graphics that are related in subject matter.

39. The absorbent article of claim 37 further comprising an outer cover graphic that is related in subject matter to the hidden graphic.

40. An absorbent article defining a longitudinal axis, a transverse axis, front and back longitudinally spaced waist regions, a crotch region which extends between and interconnects the front and back waist regions, an inner surface, and an opposite outer surface, the absorbent article comprising a fastening system that comprises first and second fastening components disposed on the inner surface in the back waist region and first and second mating fastening component disposed on the outer surface in the front waist region, each of the mating fastening components having a length dimension measured parallel to the longitudinal axis that is equal to or greater than a width dimension measured parallel to the transverse axis, and at least one of the mating fastening components comprising a freeform graphic that forms a hidden graphic when the first and second fastening components are engaged with the first and second mating fastening components.

41. The absorbent article of claim 40, wherein the mating fastening components have a length-to-width ratio of about 2 or greater.

42. The absorbent article of claim 40, wherein the fastening components and the mating fastening components each have a length-to-width ratio of about 5 or greater.

43. The absorbent article of claim 40, further comprising opposite pairs of side panels disposed in each of the first and second waist regions, the first and second fastening components attached to one pair of side panels and first and second mating fastening components attached to the second pair of side panels.

44. The absorbent article of claim 40, wherein the fastening components and the mating fastening components comprise graphics that are related in subject matter.

45. The absorbent article of claim 40, further comprising an outer cover graphic that is related in subject matter to the hidden graphic.

46. An absorbent article defining a longitudinal axis, a transverse axis, first and second longitudinally spaced waist regions, and a crotch region which extends between and interconnects the first and second waist regions, the absorbent article comprising:

an absorbent chassis comprising an outer cover and an outer cover graphic;

first and second fastening components disposed in the first waist region and comprising mechanical fastening elements; and at least one mating fastening component bonded to the outer cover in the second waist region, the at least one mating fastening component comprising mechanical fastening elements adapted to releasably engage the fastening components, at least one of the fastening components or the at least one mating fastening component comprising a graphic defining a hidden graphic, the outer cover graphic and the hidden graphic being related in subject matter.

47. The absorbent article of claim 46, wherein the outer cover graphic comprises a pictorial image and the hidden graphic comprises a text message.

48. The absorbent article of claim 46, wherein outer cover graphic and hidden graphic each comprise pictorial images that illustrate different sizes, shapes, colors of a common object.

49. The absorbent article of claim 48, wherein outer cover graphic and hidden graphic each comprise pictorial images that illustrate one and the other respectively of two objects that are commonly associated with one another.

50. The absorbent article of claim 48, wherein outer cover graphic and hidden graphic each comprise pictorial images that illustrate respectively geometrically mating or engaging elements.

51. An absorbent article defining a longitudinal axis, a transverse axis, front and back longitudinally spaced waist regions, and a crotch region which extends between and interconnects the front and back waist regions, the absorbent article comprising:
an absorbent chassis;
front elastic side panels extending transversely outward from the absorbent chassis in the front waist region;
back elastic side panels extending transversely outward from the absorbent chassis in the back waist region;
a mechanical fastening system comprising first and second fastening components disposed on the front elastic side panels and first and second mating fastening components disposed on the back elastic side panels; and
a graphic located on at least one of the fastening components or mating fastening components and forming a hidden graphic when the first and second fastening components are engaged with the first and second mating fastening components.

52. The absorbent article of claim 51, wherein at least two of the fastening components and the mating fastening components comprise graphics that are related in subject matter.

53. The absorbent article of claim 51, wherein graphics are located on the fastening components and the mating fastening components and the graphics indicate where to attach the fastening components and the mating fastening components.

54. The absorbent article of claim 51, wherein at least one fastening component and at least one mating fastening component comprise substantially identical pictorial images.

55. The absorbent article of claim 51, wherein the absorbent chassis comprises an outer cover graphic that is related in subject matter to the hidden graphic.

56. The absorbent article of claim 55, wherein the outer cover graphic comprises a pictorial image and the hidden graphic comprises a text message.

57. The absorbent article of claim 56, wherein outer cover graphic and hidden graphic each comprise pictorial images.

58. A method of making packages of absorbent articles, comprising:
providing an absorbent article comprising an absorbent chassis defining a longitudinal axis, a transverse axis, first and second longitudinally spaced waist regions, and a crotch region which extends between and interconnects the first and second waist regions, the absorbent chassis comprising a bodyside liner, an outer cover, and an absorbent assembly disposed between the bodyside liner and the outer cover;
creating a graphic on the absorbent chassis;
attaching first and second fastening components to the absorbent chassis in the first waist region;
attaching at least one mating fastening component to the absorbent chassis in the second waist region, the fastening components adapted to releasably engage the at least one mating fastening component;
releasably engaging the first and second fastening components with the at least one mating fastening component to define an overlap region of the first and second waist regions, the graphic disposed in the overlap region to define a hidden graphic;
assembling a plurality of absorbent articles having hidden graphics; and
placing the assemblage of absorbent articles having hidden graphics in a bag.

59. The method of claim 58, further comprising disposing the hidden graphic on an inner surface of the first waist region.

60. The method of claim 58, further comprising disposing the hidden graphic on one of the fastening components.

61. The method of claim 58, further comprising disposing the hidden graphic on the at least one mating fastening component.

62. The method of claim 58, further comprising disposing the hidden graphic in close proximity to and transversely outward from the mating fastening component.

63. The method of claim 59, further comprising providing the outer cover with an outer cover graphic.

64. The method of claim 63, wherein the outer cover graphic is related in subject matter to the hidden graphic.

65. The absorbent article of claim 64, wherein the outer cover graphic comprises a pictorial image and the hidden graphic comprises a text message.

66. The absorbent article of claim 64, wherein the outer cover graphic and hidden graphic each comprise text messages.

67. The absorbent article of claim 64, wherein outer cover graphic and hidden graphic each comprise pictorial images.

* * * * *